(12) United States Patent
Miller et al.

(10) Patent No.: US 8,062,483 B2
(45) Date of Patent: Nov. 22, 2011

(54) SEPARATION OF CHLOROSILANES

(75) Inventors: David Clay Miller, Madison, IN (US);
Jonathan David Wineland, Bedford, KY (US); Ora L. Flaningam, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 685 days.

(21) Appl. No.: 12/096,197

(22) PCT Filed: Dec. 6, 2006

(86) PCT No.: PCT/US2006/046809
§ 371 (c)(1),
(2), (4) Date: Sep. 15, 2008

(87) PCT Pub. No.: WO2007/067723
PCT Pub. Date: Jun. 14, 2007

(65) Prior Publication Data
US 2009/0026062 A1    Jan. 29, 2009

Related U.S. Application Data

(60) Provisional application No. 60/742,690, filed on Dec. 6, 2005.

(51) Int. Cl.
*B01D 3/34* (2006.01)
*C07F 7/00* (2006.01)

(52) U.S. Cl. .......................... 203/57; 556/466

(58) Field of Classification Search ............... 203/58, 203/59, 60, 67, 99, 50, 57; 556/466
See application file for complete search history.

(56) References Cited

U.S. PATENT DOCUMENTS

| | | | |
|---|---|---|---|
| 2,388,575 A * | 11/1945 | Sauer et al. | 203/60 |
| 2,752,379 A | 6/1956 | Wagner at al. | |
| 3,007,956 A * | 11/1961 | Linville et al. | 556/466 |
| 3,624,166 A * | 11/1971 | Fuhrmann et al. | 570/263 |
| 3,658,657 A * | 4/1972 | Bursack et al. | 203/51 |
| 4,402,796 A * | 9/1983 | Marko et al. | 203/43 |
| 4,402,797 A | 9/1983 | Halm et al. | |
| 4,411,740 A | 10/1983 | Flaningam et al. | |

* cited by examiner

*Primary Examiner* — Glenn Caldarola
*Assistant Examiner* — Patrick McCarty
(74) *Attorney, Agent, or Firm* — Matthew T. Fewkes

(57) ABSTRACT

Crude chlorosilane streams containing lower-boiling chlorosilanes and higher-boiling chlorosilanes are separated by contacting them with a distillation aid. The lower-boiling chlorosilanes are separated from the crude chlorosilane stream, and then the distillation aid and the higher-boiling chlorosilanes are separated from one another. The distillation aid is a mono-cyano-substituted organic compound, a nitro-substituted organic compound, a mono-cyano-substituted organosilicon compound, a nitro-substituted organosilicon compound, or a mixture thereof. These distillation aids increase the relative volatility of crude chlorosilane streams such as methyltrichlorosilane and dimethyldichlorosilane resulting in improved separation at lower capital and/or fixed costs.

14 Claims, 3 Drawing Sheets

SEPARATION OF CHLOROSILANES

CROSS-REFERENCE TO RELATED APPLICATIONS

This application is a U.S. national stage filing under 35 U.S.C. §371 of PCT Application No. PCT/US06/046809 filed on Dec. 6, 2006, currently pending, which claims the benefit of U.S. Provisional Patent Application No. 60/742,690 filed Dec. 6, 2005, under 35 U.S.C. §119 (e). PCT Application No. PCT/US06/046809 and U.S. Provisional Patent Application No. 60/742,690 are hereby incorporated by reference.

STATEMENT REGARDING FEDERALLY SPONSORED RESEARCH

NONE

BACKGROUND OF THE INVENTION

This invention is directed to a method of separating crude chlorosilane streams containing mixtures of close-boiling chlorosilanes with a distillation aid that is a mono-cyano-substituted organic compound, a nitro-substituted organic compound, a mono-cyano-substituted organosilicon compound, a nitro-substituted organosilicon compound, or a mixture thereof. Lower-boiling chlorosilanes are removed from the crude chlorosilane stream, and the distillation aid and the higher-boiling chlorosilanes are separated from one another.

During the reaction of methyl chloride with silicon, a crude chlorosilane stream is produced. These are normally separated by distillation. Two of the largest volume chlorosilanes are dimethyldichlorosilane $Me_2SiCl_2$ and methyltrichlorosilane $MeSiCl_3$. In order to prepare satisfactory siloxane polymers from dimethyldichlorosilane, it is sometimes necessary that the methyltrichlorosilane content of the dimethyldichlorosilane be reduced to trace amounts. The boiling points of methyltrichlorosilane (66.1° C.) and dimethyldichlorosilane (70.1° C.) are sufficiently close that distillation columns of 200 stages or more are required to satisfactorily separate these materials in commercial operations. Consequently, a large capital investment is required in order to install these columns, and it would be highly desirable to reduce this capital investment. Also, a large column generally requires more energy to operate than a smaller column. Careful fractional distillation is also employed by the organosilicon industry to separate other close-boiling chlorosilanes. The present invention is therefore directed to a method of separating crude chlorosilane streams containing close-boiling chlorosilanes such as dimethyldichlorosilane and methyltrichlorosilane which uses smaller distillation columns, and that requires less energy, thereby reducing the capital investment necessary in basic chlorosilane plants.

It is known in the art to use dinitrile compounds which form a separate extract phase that is enriched in difunctional chlorosilane, or dinitrile compounds are used with an additional non-polar wash solvent with low miscibility with the dinitriles, or dinitrile compounds are used as an extraction solvent. By contrast, the present invention does not involve formation of an extract phase with dinitriles, the use of dinitriles with an additional low miscibility non-polar wash solvents, nor does it utilize di-nitrile compounds as an extraction solvent. The present invention uses a mono-cyano-substituted organic compound, a nitro-substituted organic compound, a mono-cyano-substituted organosilicon compound, a nitro-substituted organosilicon compound, or a mixture thereof for separating crude chlorosilane streams containing mixtures of close-boiling chlorosilanes. Mono-cyano-substituted organic compounds are lower boiling materials with normal boiling points that are more than 100° C. lower than the corresponding dinitrile compounds. This distinction allows the separation steps to be conducted at correspondingly lower temperatures, thus avoiding the risk of decomposing the distillation aid in operation.

BRIEF SUMMARY OF THE INVENTION

The invention relates to a method of separating crude chlorosilane streams of lower-boiling chlorosilanes and higher-boiling chlorosilanes. The method comprises contacting the crude chlorosilane stream with a distillation aid selected from the group consisting of mono-cyano-substituted organic compounds, nitro-substituted organic compounds, mono-cyano-substituted organosilicon compounds, nitro-substituted organosilicon compounds, and mixtures thereof. The lower-boiling chlorosilanes are recovered from the crude chlorosilane stream. The distillation aid is separated from the higher-boiling chlorosilanes.

BRIEF DESCRIPTION OF THE DRAWINGS

FIG. 1 is a plot of $MeSiCl_3$/$Me_2SiCl_2$ relative volatility, with and without benzonitrile added, versus $MeSiCl_3$ concentration.

FIG. 2 is a plot of the normalized column re-boiler duty, i.e., the energy requirement, versus normalized column stages, i.e., size, each normalized versus a base case with no distillation aid.

FIG. 3 is a plot of the normalized residual $MeSiCl_3$ in the $Me_2SiCl_2$ product coming out of the bottom of the distillation column versus the weight percent of benzonitrile in the column, normalized versus a base case with no distillation aid.

DETAILED DESCRIPTION OF THE INVENTION

Figure 1:
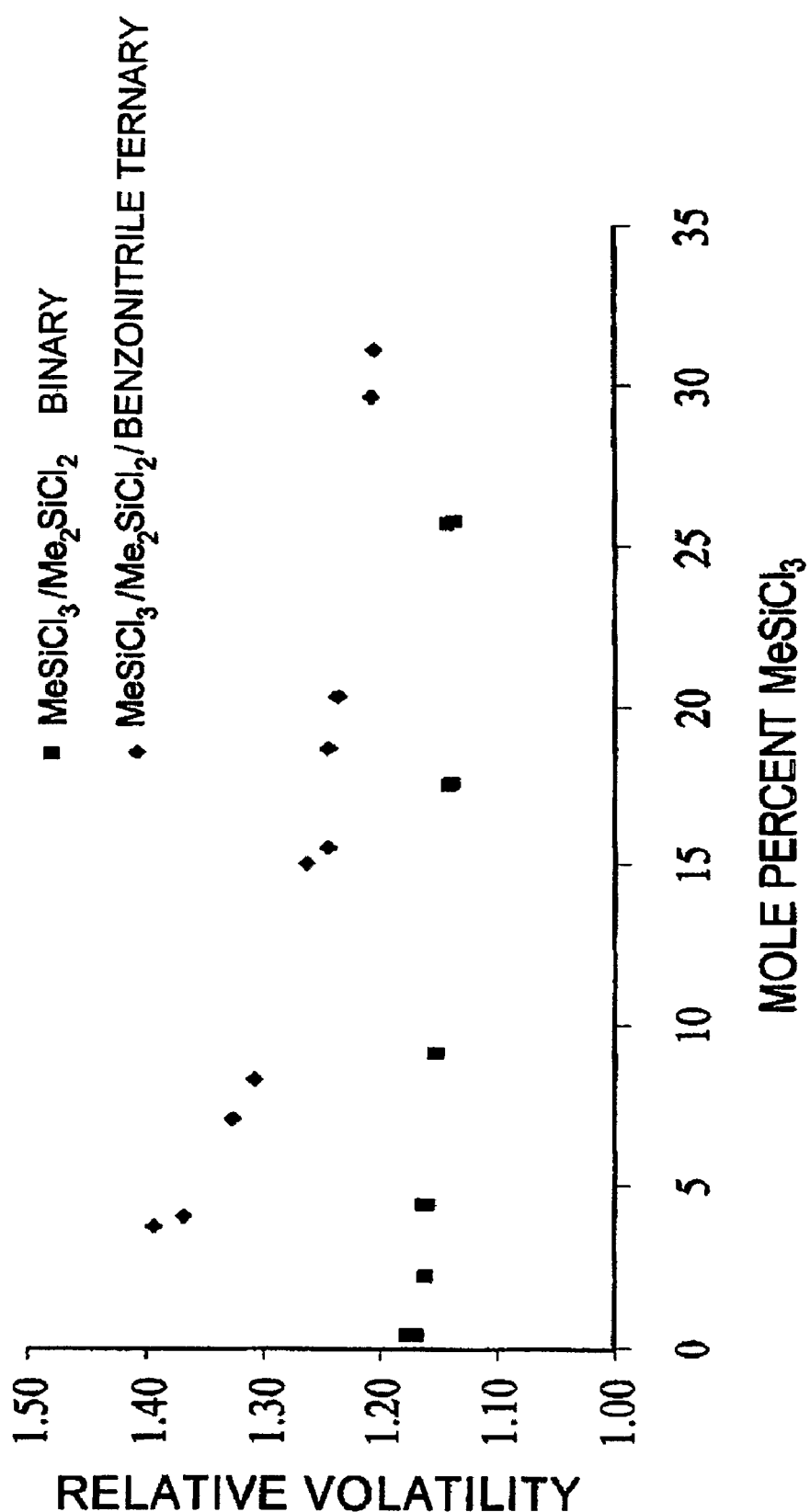
FIG. 1 is a graphical representation of the $MeSiCl_3$/$Me_2SiCl_2$ relative volatility enhancement which can be obtained according to the invention. In particular.
Figure 2:
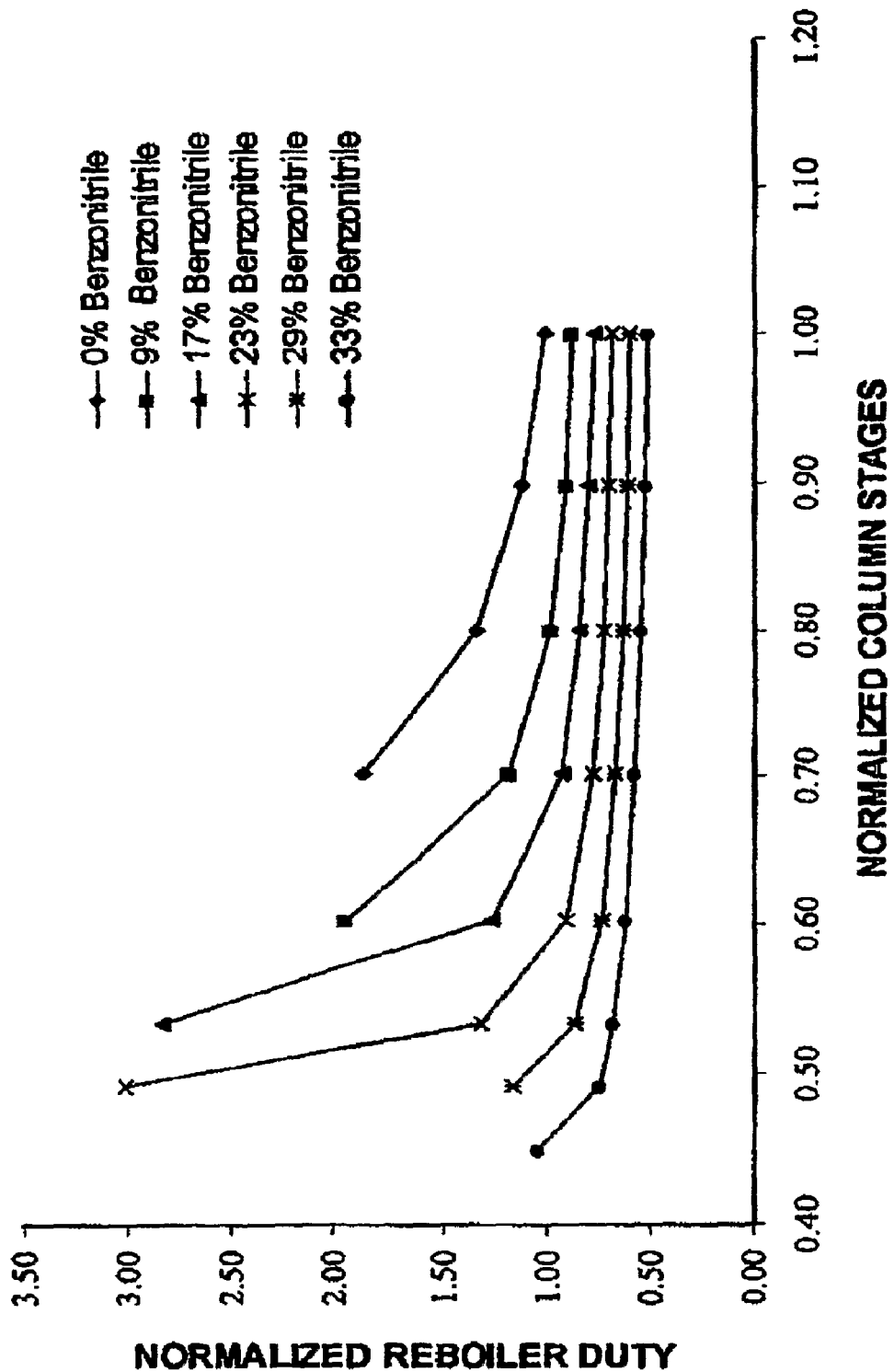
FIG. 2 is a graphical representation showing the reduction in distillation column stages and re-boiler duty, i.e., capital and energy savings, that can be obtained according to the invention. In particular.
Figure 3:
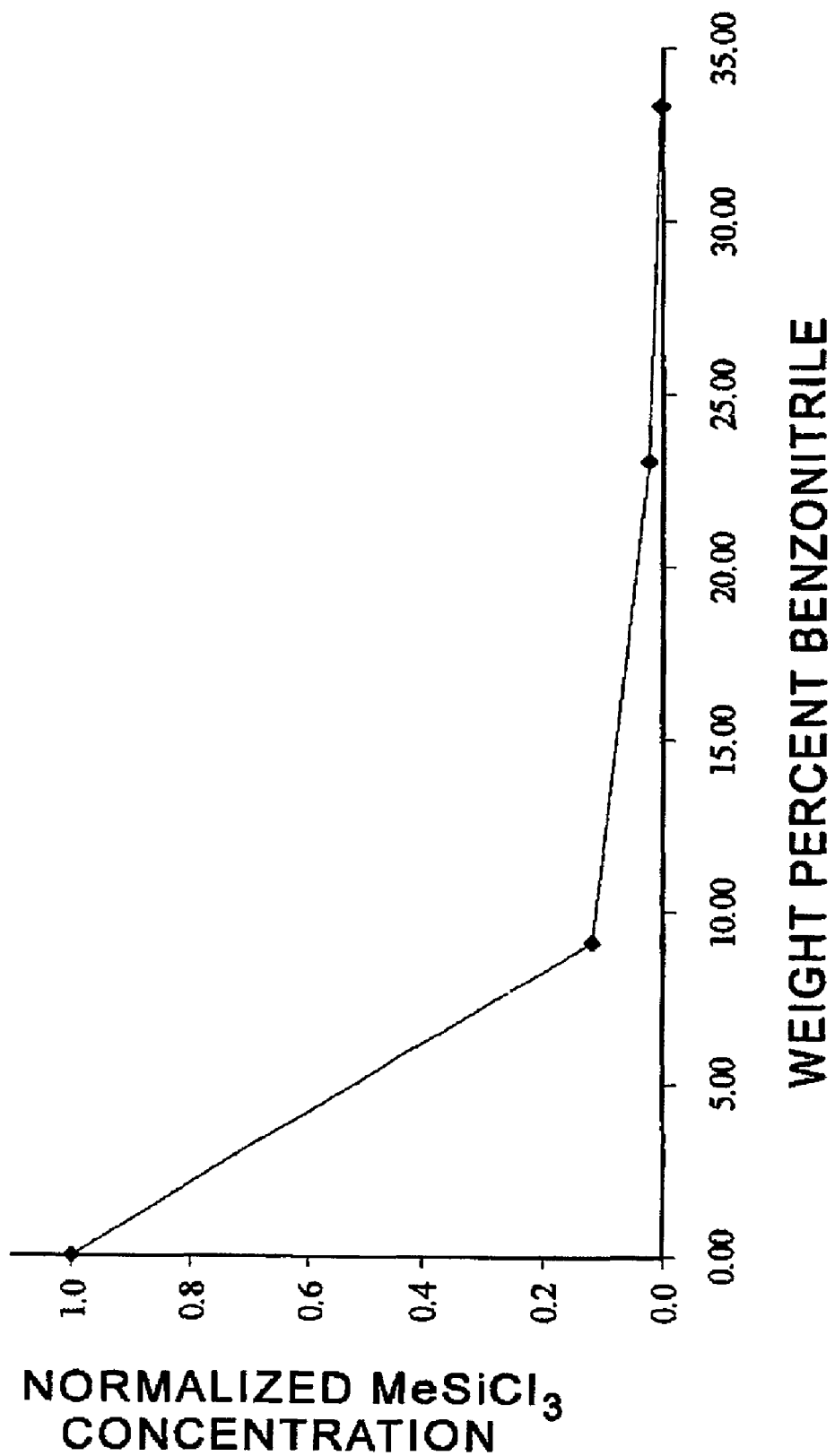
FIG. 3 is a graphical representation showing the improved $Me_2SiCl_2$ purity that can be obtained according to the invention. In particular.

The invention relates to a method of separating crude chlorosilane streams containing mixtures of chlorosilanes. The method comprises contacting the crude chlorosilane stream with a distillation aid, separating the lower-boiling chlorosilanes from the crude chlorosilane stream and separating the distillation aid from the higher-boiling chlorosilanes.

As used herein, crude chlorosilane streams means mixtures of lower-boiling chlorosilanes and higher-boiling chlorosilanes. In one embodiment, the crude chlorosilane stream contains close-boiling chlorosilanes. Representative examples of crude chlorosilane streams include those produced in the so-called direct process reaction of methyl chloride and silicon and mixtures of chlorosilane products utilized in the organosilicon industry. Another example of a crude chlorosilane stream is one containing methyltrichlorosilane and dimethyldichlorosilane. Still other examples of crude close-boiling chlorosilane streams which can be separated by the process of the invention include (i) crude streams containing dimethyldichlorosilane (b.p. ~70.1° C.) and ethyldichlorosilane (74.6° C.) $C_2H_5SiHCl_2$, (ii) crude streams containing phenyltrichlorosilane (201° C.) $C_6H_5SiCl_3$ and phenylmethyldichlorosilane (205.6° C.) $(CH_3)(C_6H_5)SiCl_2$, and (iii) crude streams containing methylvinyldichlorosilane (92.3° C.) $CH_2=CH(CH_3)SiCl_2$ and vinyltrichlorosilane (93° C.) $CH_2=CHSiCl_3$. As used herein, close-boiling chlorosilanes is intended to mean chlorosilanes which have boiling points within about 25° C. of each other at atmospheric pressure, alternatively within about 10° C. of each other at atmospheric pressure.

Compounds suitable for use herein as the distillation aid include mono-cyano-substituted organic compounds, nitro-substituted organic compounds, mono-cyano-substituted organosilicon compounds, nitro-substituted organosilicon compounds, or mixtures thereof. The distillation aid should be a liquid at the separation temperature and preferably at ambient temperature. Additionally, the distillation aid should generally have a boiling point higher than that of the chlorosilanes to be separated, and should generally not react with the chlorosilanes nor decompose at the maximum separation temperatures employed.

Some examples of mono-cyano-substituted organic compounds that can be used include acrylonitrile, benzonitrile, butyronitrile, caprylonitrile, propionitrile, 2-methyl-2-butenenitrile, 2-pentenenitrile, 4-pentenenitrile, and cyanoacetate esters. Some preferred examples are caprylonitrile $CH_3(CH_2)_6CN$ and benzonitrile $C_6H_5CN$.

Some examples of mono-cyano-substituted organosilicon compounds that can be used include 3-cyanopropyldimethylchlorosilane $N\equiv C-CH_2CH_2CH_2Si(CH_3)_2Cl$, 3-cyanopropylmethyldichlorosilane $N\equiv C-CH_2CH_2CH_2Si(CH_3)Cl_2$, 3-cyanopropylphenyldichlorosilane $N\equiv C-CH_2CH_2CH_2SiC_6H_5Cl_2$, 3-cyanopropyltrichlorosilane $N\equiv C-CH_2CH_2CH_2SiCl_3$, and 3-cyanoethyltrichlorosilane $N\equiv C-CH_2CH_2SiCl_3$.

Some examples of nitro-substituted organic compounds that can be used include nitroethane $C_2H_5NO_2$, and 1-nitropropane $CH_3CH_2CH_2NO_2$. A preferred example is 1-nitropropane.

Some examples of nitro-substituted organosilicon compounds that can be used include trichloro(nitropropyl)silane $Cl_3Si(CH_2)_3NO_2$, methyldichloro(nitropropyl)silane $CH_3Cl_2Si(CH_2)_3NO_2$, ethyldichloro(nitropropyl)silane $C_2H_5Cl_2Si(CH_2)_3NO_2$, and methyldichloro(nitroethyl)silane $CH_3Cl_2Si(CH_2)_2NO_2$.

The distillation aid should generally be as dry as possible to minimize hydrolysis of the chlorosilanes. One method of removing residual water from the distillation aid is to dry the distillation aid over molecular sieves. To prevent the reintroduction of water, the dried distillation aid should not be exposed to water vapor.

It has been found that any concentration of distillation aid enhances the separation of close-boiling chlorosilanes by promoting, in the case of crude chlorosilane streams containing dimethyldichlorosilane (70.1° C.) and methyltrichlorosilane (66.1° C.), the removal of methyltrichlorosilane from the crude chlorosilane stream.

According to the method, the crude chlorosilane streams are contacted with a distillation aid, and the lower-boiling chlorosilanes are separated from the crude chlorosilane stream. The separation can be carried out in any suitable manner such as by mixing the crude chlorosilane stream and the distillation aid in a retort, and then heating the mixture to remove the lower-boiling chlorosilane. Alternatively, the vapors of the mixed chlorosilanes (crude chlorosilane) can be passed into the distillation aid which is maintained at a temperature above the boiling point of the lower-boiling chlorosilane.

In one method, the distillation aid is passed counter-currently to the vapors of the mixed silanes in a distillation column or tower. The temperature of the column or tower should be regulated so that liquid distillation aid flowing to the column or tower comes into contact with the vapors of the mixed chlorosilanes rising in the column or tower, and with the condensed vapors on each tray or stage in the column or tower below the distillation aid feed point.

After removal of the lower-boiling chlorosilane, the distillation aid and the higher-boiling chlorosilane can be separated in any suitable manner such as by gas-liquid chromatography, distillation, or flash distillation.

The method of the instant invention can be carried out at above atmospheric pressure, at atmospheric pressure, or at reduced pressure. It is preferred that the pressure should be sufficiently low so that the re-boiler temperature is not high enough to thermally decompose the distillation aid to a significant extent.

In large scale commercial operations, the distillation aid is employed in amounts which reduce the required distillation reflux ratio and corresponding energy requirements on the one hand, while minimizing the required distillation column size (contacting stages and column diameter) to reduce capital costs on the other hand. As is known in the art, this requires balancing capital equipment costs, energy costs and distillation aid costs, along with business expectations for return on investment. Examples of workable distillation aid concentrations are up to 50 weight % concentration of distillation aid in the chlorosilane mixture, or alternately 1% to 50 weight % concentration of distillation aid in the chlorosilane mixture, or alternately between 25% and 45 weight % concentration of distillation aid in the chlorosilane mixture.

The invention can be carried out in the presence of other silanes which may be present in the crude chlorosilane streams. For example, the presence of silicon tetrachloride $SiCl_4$, trimethylchlorosilane $(CH_3)_3SiCl$, methyldichlorosilane $CH_3SiHCl$, and dimethylchlorosilane $(CH_3)_2SiHCl$, do not inhibit the removal of the methyltrichlorosilane from a crude chlorosilane streams containing dimethyldichlorosilane and methyltrichlorosilane, produced by the direct reaction of silicon metal and methyl chloride. These other silanes will distill before, or along with methyltrichlorosilane.

EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. In each example embodiment, a mono-cyano or nitro-functional distillation aid was utilized which did not form a separate extract phase, was miscible with the crude chlorosilane stream and which did not employ an additional non-polar solvent.

Example 1

Relative Volatility Screening

One gram of a 50/50 mole percent mixture of $MeSiCl_3$ and $Me_2SiCl_2$, and one gram of the mono-cyano-functional compound or nitro-functional compound to be tested were weighed into a 20 mL headspace vial at room temperature, and allowed to equilibrate. The headspace and liquid phases were analyzed by a gas chromatograph equipped with a thermal conductivity detector (GC-TCD) to determine the relative volatility of the mixture according to the following equation:

$$\alpha = \{[MeSiCl_3]_v[Me_2SiCl_2]_l\} \div \{[MeSiCl_3]_l[Me_2SiCl_2]_v\}$$

where $\alpha$ is the relative volatility, Me is methyl and v and l are the measured mole percent concentrations of $MeSiCl_3$ and $Me_2SiCl_2$ in the vapor and liquid phases, respectively. The relative volatility of a 50/50 mole percent mixture of $MeSiCl_3$ and $Me_2SiCl_2$ was measured in the same way as a control for comparison. The results are shown in Table 1. Values for α which are greater than the control value show that the corresponding example compounds when contacted with crude chlorosilanes will enhance the recovery of the lower boiling chlorosilane ($MeSiCl_3$ in this example) from the crude chlorosilane stream. Since the example compounds can be chosen with normal boiling points which are significantly different from the chlorosilane boiling points, separation of the distillation aid from the higher boiling chlorosilanes is easily accomplished, for example, through distillation.

TABLE 1

| Mono-Cyano- or Nitro-Functional Distillation Aid | Normal Boiling Point °C. | Measured Relative Volatility | Percent Enhancement |
|---|---|---|---|
| Control - No Distillation Aid | | 1.20 | None |
| 3-Cyanopropyldimethylchlorosilane, N≡CCH₂CH₂CH₂Si(CH₃)₂Cl | 230-235 | 1.24 | 3.3 |
| 3-Cyanopropyltrichlorosilane, (Cl)₃Si(CH₂)₃CN | 237-238 | 1.31 | 9.2 |
| 4-pentenenitrile, (CH₂)=CH(CH₂)₂CN | 140 | 1.40 | 16.7 |
| Caprylonitrile, CH₃(CH₂)₆CN | 198-200 | 1.30 | 8.3 |
| Benzonitrile, C₆H₅CN | 191 | 1.31 | 9.2 |
| Methyl Cyanoacetate, (CH₃)O₂C(CH₂)CN | 204-207 | 1.47 | 22.5 |
| 1-Nitropropane, CH₃(CH₂)₂NO₂ | 131-132 | 1.37 | 14.2 |
| 2-Nitropropane, (CH₃)₂CHNO₂ | 120 | 1.36 | 13.3 |
| 1-Nitrobutane, CH₃(CH₂)₃NO₂ | 152-153 | 1.32 | 10.0 |
| 2-Methyl-2-Nitropropane, (CH₃)₃CNO₂ | 126-127 | 1.30 | 8.3 |
| Nitrocyclopentane, (CH₂)₄CHNO₂ | 180 | 1.38 | 15.0 |
| Nitrobenzene, C₆H₅NO₂ | 210-211 | 1.35 | 12.5 |

Example 2

Relative Volatility Enhancement Screening

Approximately 1.5 grams of a 10/90 mole percent mixture of $MeSiCl_3$ and $Me_2SiCl_2$, were weighed into 20-mL headspace vials. Varying amounts of benzonitrile were added along with an amount of inert glass beads required to keep the total headspace volume in the vials constant. The vials were allowed to equilibrate at room temperature and the headspace and liquid phases were analyzed by a GC-TCD to determine the relative volatility of the mixture according to the equations given in example 1 above. The relative volatility of a 10/90 mole percent mixture of $MeSiCl_3$ and $Me_2SiCl_2$ was measured in the same way as a control for comparison. The results are shown in Table 2 and show that increasing amounts of additive enhance relative volatility.

TABLE 2

| Benzonitrile Concentration, wt % | Measured Relative Volatility |
|---|---|
| 0 (control) | 1.17 |
| 10 | 1.23 |
| 15 | 1.28 |
| 25 | 1.30 |
| 38 | 1.30 |

Example 3

$MeSiCl_3/Me_2SiCl_2$/Benzonitrile Ternary Vapor-Liquid Extraction (VLE)

Relative volatilities for $MeSiCl_3/Me_2SiCl_2$ were calculated from rigorous VLE data collected for mixtures of $MeSiCl_3/Me_2SiCl_2$/Benzonitrile, where the Benzonitrile/$Me_2SiCl_2$ was varied between 10:90 and 50:50. The relative volatilities for the ternary system were then compared to results obtained for the $MeSiCl_3/Me_2SiCl_2$ binary system. Graphical representation of the results is shown in FIG. 1. It is apparent from FIG. 1 that the addition of benzonitrile resulted in relative volatility enhancements of $MeSiCl_3$ to $Me_2SiCl_2$ ranging from approximately 18 percent at low $MeSiCl_3$ concentrations to approximately 6 percent at high $MeSiCl_3$ concentrations. This demonstrates that the benzonitrile significantly enhances separation capability to recover lower-boiling $MeSiCl_3$ from higher-boiling $Me_2SiCl_2$ chlorosilane species through, for example, distillation.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A method of separating crude chlorosilane streams of lower-boiling chlorosilanes and higher-boiling chlorosilanes comprising:
   (A) contacting the crude chlorosilane stream, wherein the crude chlorosilane stream contains dimethyldichlorosilane and methyltrichlorosilane, with a distillation aid selected from the group consisting of mono-cyano-substituted organic compounds, nitro-substituted organic compounds, mono-cyano-substituted organosilicon compounds, nitro-substituted organosilicon compounds, and mixtures thereof;
   (B) recovering the lower-boiling chlorosilanes from the crude chlorosilane stream; and
   (C) separating the distillation aid and the higher-boiling chlorosilanes.

2. A method according to claim 1 in which the distillation aid is selected from the group consisting of: acrylonitrile, benzonitrile, butyronitrile, caprylonitrile, propionitrile, 2-methyl-2-butenenitrile, 2-pentenenitrile, 4-pentenitrile, 3-cyanopropyldimethylchlorosilane, 3-cyanopropylmethyldichlorosilane, 3-cyanopropylphenyldichlorosilane, 3-cyanopropyltrichlorosilane, 3-cyanoethyltrichlorosilane, nitroethane, 1-nitropropane, trichloro(nitropropyl)silane, methyldichloro(nitropropyl)silane, ethyldichloro(nitropropyl)silane, methyldichloro(nitroethyl)silane and mixtures thereof.

3. A method according to claim 1 in which the distillation aid is selected from the group consisting of: acrylonitrile, benzonitrile, butyronitrile, caprylonitrile, propionitrile, 2-methyl-2-butenenitrile, 2-pentenenitrile, 4-pentenitrile, 3-cyanopropyldimethylchlorosilane, 3-cyanopropylmethyldichlorosilane, 3-cyanopropylphenyldichlorosilane, 3-cyanopropyltrichlorosilane, 3-cyanoethyltrichlorosilane, 1-nitropropane, trichloro(nitropropyl)silane, methyldichloro(nitropropyl)silane, ethyldichloro(nitropropyl)silane, methyldichloro(nitroethyl)silane and mixtures thereof.

4. A method according to claim 1 in which the distillation aid is selected from the group consisting of: benzonitrile, caprylonitrile, 1-nitropropane and mixtures thereof.

5. A method according to claim 1 in which the distillation aid is employed at up to 50% by weight concentration of distillation aid in the crude chlorosilane stream.

6. A method according to claim 1 in which the distillation aid is employed at 1% to 50% by weight concentration of distillation aid in the crude chlorosilane stream.

7. A method according to claim 1 in which the distillation aid is employed at 25% to 45% by weight concentration of distillation aid in the crude chlorosilane stream.

8. A method of separating crude chlorosilane streams of lower-boiling chlorosilanes and higher-boiling chlorosilanes comprising:
(A) contacting the crude chlorosilane stream, wherein the crude chlorosilane stream is selected from the group consisting of streams containing dimethyldichlorosilane and ethyldichlorosilane, streams containing phenyltrichlorosilane and phenylmethyldichlorosilane, and streams containing methylvinyldichlorosilane and vinyltrichlorosilane, with a distillation aid selected from the group consisting of mono-cyano-substituted organic compounds, nitro-substituted organic compounds, mono-cyano-substituted organosilicon compounds, nitro-substituted organosilicon compounds, and mixtures thereof;
(B) recovering the lower-boiling chlorosilanes from the crude chlorosilane stream; and
(C) separating the distillation aid and the higher-boiling chlorosilanes.

9. A method according to claim 8 in which the distillation aid is selected from the group consisting of: acrylonitrile, benzonitrile, butyronitrile, caprylonitrile, propionitrile, 2-methyl-2-butenenitrile, 2-pentenenitrile, 4-pentenitrile, 3-cyanopropyldimethylchlorosilane, 3-cyanopropylmethyldichlorosilane, 3-cyanopropylphenyldichlorosilane, 3-cyanopropyltrichlorosilane, 3-cyanoethyltrichlorosilane, nitroethane, 1-nitropropane, trichloro(nitropropyl)silane, methyldichloro(nitropropyl)silane, ethyldichloro(nitropropyl)silane, methyldichloro(nitroethyl)silane and mixtures thereof.

10. A method according to claim 8 in which the distillation aid is selected from the group consisting of: acrylonitrile, benzonitrile, butyronitrile, caprylonitrile, propionitrile, 2-methyl-2-butenenitrile, 2-pentenenitrile, 4-pentenitrile, 3-cyanopropyldimethylchlorosilane, 3-cyanopropylmethyldichlorosilane, 3-cyanopropylphenyldichlorosilane, 3-cyanopropyltrichlorosilane, 3-cyanoethyltrichlorosilane, 1-nitropropane, trichloro(nitropropyl)silane, methyldichloro(nitropropyl)silane, ethyldichloro(nitropropyl)silane, methyldichloro(nitroethyl)silane and mixtures thereof.

11. A method according to claim 8 in which the distillation aid is selected from the group consisting of: benzonitrile, caprylonitrile, 1-nitropropane and mixtures thereof.

12. A method according to claim 8 in which the distillation aid is employed at up to 50% by weight concentration of distillation aid in the crude chlorosilane stream.

13. A method according to claim 8 in which the distillation aid is employed at 1% to 50% by weight concentration of distillation aid in the crude chlorosilane stream.

14. A method according to claim 8 in which the distillation aid is employed at 25% to 45% by weight concentration of distillation aid in the crude chlorosilane stream.

* * * * *